United States Patent
Hiraku et al.

(10) Patent No.: US 7,063,785 B2
(45) Date of Patent: Jun. 20, 2006

(54) PUMP FOR LIQUID CHROMATOGRAPHY

(75) Inventors: Kenji Hiraku, Chiyoda (JP); Kunihiko Takao, Tsuchiura (JP); Hironori Kaji, Hitachinaka (JP); Masahito Ito, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 124 days.

(21) Appl. No.: 10/902,028

(22) Filed: Jul. 30, 2004

(65) Prior Publication Data
US 2005/0023205 A1 Feb. 3, 2005

(30) Foreign Application Priority Data
Aug. 1, 2003 (JP) ............................. 2003-205234

(51) Int. Cl.
*B01D 15/08* (2006.01)
(52) U.S. Cl. .................. 210/198.2; 210/656; 210/101; 417/245; 417/254; 417/265; 417/426
(58) Field of Classification Search ............... 210/656, 210/659, 101, 198.2; 417/44.2, 245, 254, 417/265, 426
See application file for complete search history.

(56) References Cited

U.S. PATENT DOCUMENTS

| | | | | |
|---|---|---|---|---|
| 1,270,493 A | * | 6/1918 | Campodonico | 417/211 |
| 2,274,224 A | * | 2/1942 | Vickers | 417/250 |
| 2,373,779 A | * | 4/1945 | Harry | 417/265 |
| 4,233,156 A | * | 11/1980 | Tsukada et al. | 210/101 |
| 4,600,365 A | * | 7/1986 | Riggenmann | 417/246 |
| 4,681,513 A | * | 7/1987 | Saito et al. | 417/2 |
| 4,752,385 A | * | 6/1988 | Wilson | 210/101 |
| 4,808,077 A | * | 2/1989 | Kan et al. | 417/2 |
| 4,810,168 A | * | 3/1989 | Nogami et al. | 417/2 |
| 4,883,409 A | * | 11/1989 | Strohmeier et al. | 417/43 |
| 4,980,059 A | * | 12/1990 | Barlow et al. | 210/198.2 |
| 5,324,175 A | * | 6/1994 | Sorensen et al. | 417/254 |
| 5,637,208 A | * | 6/1997 | Dourdeville | 210/90 |
| 5,653,876 A | * | 8/1997 | Funke | 210/198.2 |
| 5,852,231 A | * | 12/1998 | Kaji | 73/61.56 |

(Continued)

FOREIGN PATENT DOCUMENTS

JP 63-36668 3/1988

(Continued)

*Primary Examiner*—Ernest G. Therkorn
(74) *Attorney, Agent, or Firm*—Antonelli, Terry, Stout and Kraus, LLP.

(57) ABSTRACT

The invention provides a pump for liquid chromatography excellent in feeding liquid stably at an extremely low flow rate with high accuracy and in discharging bubbles at startup.

At startup, a first plunger feeds solvent at a large flow rate to discharge bubbles in a pump and to fill the solvent into the pump in a short time and in a normal operation, the first plunger is stopped and the second plunger is pushed into a second pressure chamber at a low speed to feed the solvent at a low flow rate. When the second plunger reaches full stroke, the second plunger is pulled back at a high speed and at the same time the first plunger is pushed into a first pressure chamber in synchronization with the pullback of the second plunger to control the flow rate passing a discharge passage to a constant value at all times by a controller. Further, while the second plunger feeds the solvent, the first plunger is slightly pushed into the first pressure chamber to keep pressure in the first pressure chamber at pressure equal to or less than pressure in the second pressure chamber.

10 Claims, 13 Drawing Sheets

U.S. PATENT DOCUMENTS 5,897,781 A * 4/1999 Dourdeville ................ 210/656
6,099,724 A * 8/2000 Dourdeville ............. 210/198.2
6,923,916 B1 * 8/2005 Hiraku et al. ................ 210/656

FOREIGN PATENT DOCUMENTS

JP    63-075375    5/1988

* cited by examiner

PUMP FOR LIQUID CHROMATOGRAPHY

CLAIM OF PRIORITY

The present application claims priority from Japanese application serial JP 2003-205234 filed on Aug. 1, 2003, the content of which is hereby incorporated by reference into this application.

FIELD OF THE INVENTION

The present invention relates to liquid chromatography and in particular, to a pump for liquid chromatography that is excellent in feeding liquid stably at a low flow rate.

BACKGROUND OF THE INVENTION

As a conventional pump for liquid chromatography has been known a construction in which a first plunger and a second plunger are driven independently and cooperatively by motors to reduce a pulsating flow rate (for example, see patent document 1).

Describing this construction, while the first plunger reciprocates one time, the second plunger also reciprocates one time to correct a pulsating flow rate caused by the suction of the first plunger by the operation of the second plunger. That is, in this construction, the first plunger determines a liquid flow rate and the second plunger is used for correcting the pulsating flow rate caused by the first plunger. [Patent document 1] Japanese Utility Model Laid-Open No. S63 (1988)-36668 (pages 5 to 7)

However, in the above-described conventional pump for liquid chromatography, in a case where in order to feed liquid at a low flow rate, the speed reduction ratio of a motor is increased to decrease the speed of the plunger or the diameter or stroke of the plunger is decreased, conversely, the liquid can not be fed at a large flow rate. For this reason, this pump presents a problem that it takes much time to fill solvent into the passage of a measurement system on the downstream side of the pump at the startup of test and a problem that bubbles remaining in the pump can not be easily discharged. When the bubbles are not discharged, even if the plunger reciprocates, the plunger only compresses or expands the bubbles and cannot discharge the smallest amount of liquid. Therefore, there is presented a problem that this pump is not appropriate for constructing a pump used for an extremely low flow rate.

Moreover, a check valve for holding high pressure is generally made of a material of high hardness such as stainless steel, ruby, or ceramics. However, even if the check valve of this kind is closed, minute leakage cannot be avoided and in particular, in the case of feeding liquid at an extremely low flow, becomes a large factor to reduce a liquid feed accuracy. On the other hand, the check valve constructed of a soft material such as resin has high hermeticity and hence can minimize leakage but is not applicable because of durability. In this manner, there is presented a problem that the check valve cannot feed liquid at an extremely low flow rate with high accuracy.

SUMAMRY OF THE INVENTION

The object of the present invention is to provide a pump for liquid chromatography that can feed liquid at an extremely low flow rate of a level of 1 μL/min or less with stability and with high accuracy and can complete filling solvent or discharging bubbles at the startup of test in a short time.

A pump for liquid chromatography in accordance with the present invention includes a first pressure chamber communicating with a suction passage and a middle passage, a first plunger reciprocating in the first pressure chamber, a suction valve provided in the suction passage, a discharge valve provided in the middle passage, a second pressure chamber formed on the downstream side of the discharge valve and communicating with the middle passage and a discharge passage, and a second plunger reciprocating in the second pressure chamber. In this construction, the first and the second plungers are so constructed as to be driven independently by separate actuators, respectively, and the maximum flow rate by the first plunger is larger than the maximum flow rate by the second plunger and the minimum flow rate by the first plunger is smaller than the minimum flow rate by the second plunger. That is, the product of the sectional area and the maximum speed of the first plunger is larger than the product of the sectional area and the maximum speed of the second plunger, and the product of the sectional area and the minimum speed of the first plunger is smaller than the product of the sectional area and the maximum speed of the second plunger.

Further, preferably, a drain valve is provided on the downstream side of the discharge passage and the drain valve is opened at the startup of test and solvent is fed at a large flow rate by the first plunger to discharge bubbles remaining in the pressure chamber and at the same time to fill the solvent into a downstream passage. Thereafter, the drain valve is closed and the second plunger is pushed into the second pressure chamber at a low speed to feed the solvent at a low flow rate. When the second plunger reaches near full stroke, the second plunger is pulled back at a high speed and the first plunger is pushed into the first pressure chamber in synchronization with the pullback of the second plunger to control a flow rate passing a discharge passage to a constant value at all times.

Still further preferably, the time required to push the second plunger in one reciprocation stroke is equal to or more than ten times the time required to pull back the second plunger.

Still further preferably, the flow rate of liquid by the second plunger ranges from 0.1 nL/min to 50 μL/min.

Still further preferably, the amount of push of the first plunger into the first pressure chamber while the second plunger feeds the liquid is controlled to keep pressure in the first pressure chamber at pressure equal to or less than pressure in the second pressure chamber.

Still further preferably, the surface of at least one of a valve seat and a valve body constructing the discharge valve is formed of material such as resin or rubber that has hardness lower than metal.

Still further preferably, when the amount of flow rate of the pump is low particularly in a gradient operation, the second plunger is not pulled back except when the second plunger reaches a full stroke position.

DETAILED DESCRIPTION OF THE PREFERRED EMBODIMENTS

The embodiments in accordance with the invention will be described with reference to the drawings.

Figure 1:
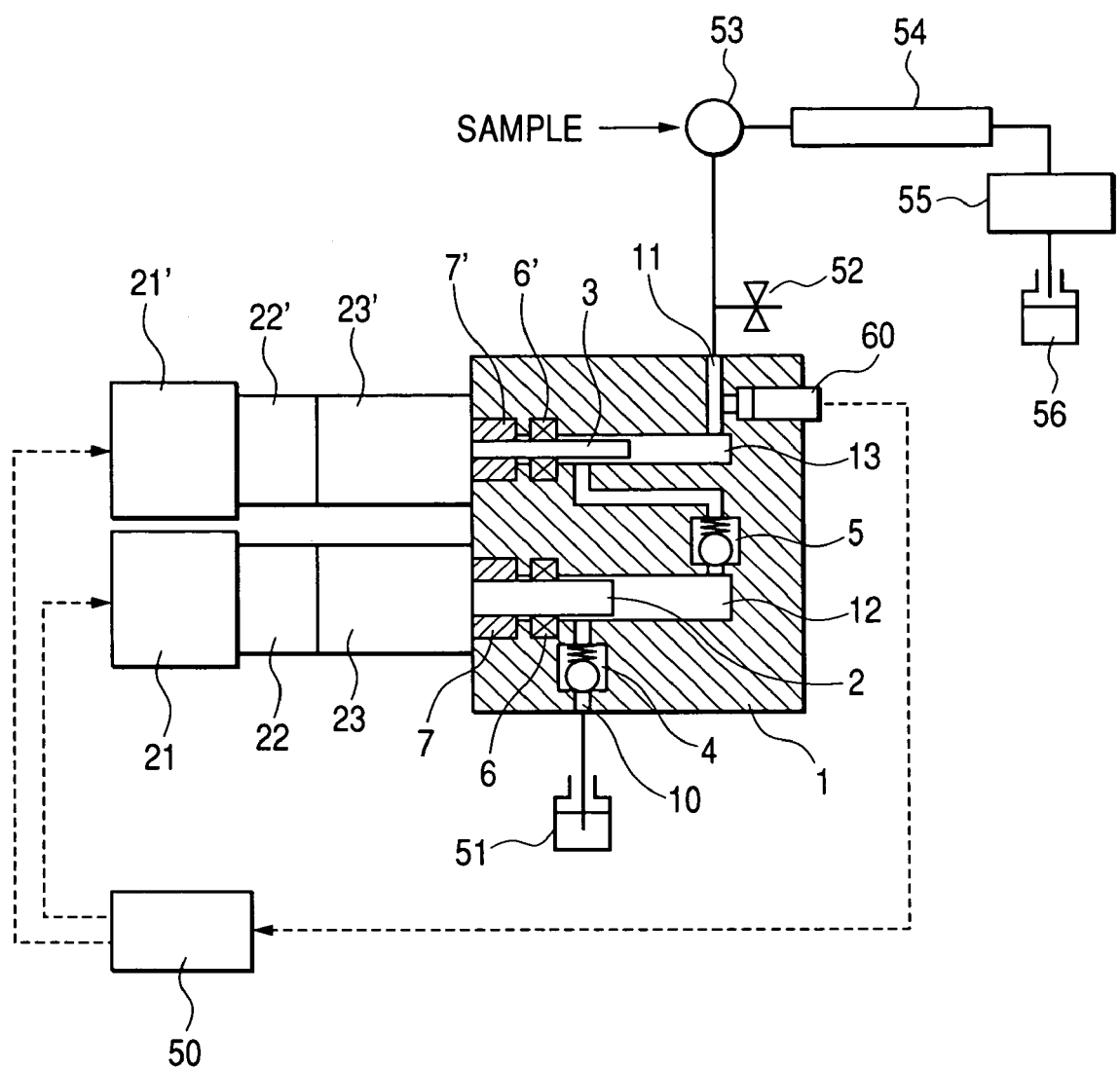
FIG. 1 is a longitudinal sectional view to show one embodiment of a pump for liquid chromatography of the invention.

The construction and operation of one embodiment in accordance with the invention will be described by use of FIG. 1 to FIG. 3. In FIG. 1, in a pump body 1 are formed a suction passage 10, a discharge passage 11, a first pressure chamber 12, and a second pressure chamber 13. In the first pressure chamber 12 and the second pressure chamber 13, a first plunger 2 and a second plunger 3 that are members for applying pressure, respectively, are slidably held by bearings 7, 7'. The suction passage 10 is provided with a suction check valve 4 and a middle passage that makes the first pressure chamber 12 communicate with the second pressure chamber 13 is provided with a discharge check valve 5. Each of the suction check valve 4 and the discharge check valve 5 is held in one direction by a spring and becomes a check valve to limit the direction in which solvent flows. The rotation of a motor 21 is reduced in speed by a speed reduction mechanism 22 and is converted to a linear motion by a direct-acting mechanism 23 to reciprocate the first plunger 2. Similarly, the second plunger 3 is also reciprocated by an actuator including a motor 21', a speed reduction mechanism 22', and a direct-acting mechanism 23'. Seals 6, 6' prevent a liquid leakage from the first pressure chamber 12 and the second pressure chamber 13, respectively. A controller 50 gives drive signals to the motors 21, 21' on the basis of the signal of a pressure sensor 60.

Solvent 51 is sucked into the pump through the suction passage 10 and is discharged from the discharge passage 11 and then a sample to be analyzed is injected by an injector 53. Mixed solution is entered into a column 54 and is separated for each component and then has components analyzed by a detector 55. The column 54 is filled with micro silica gel grains and a load pressure of about 10 MPa is generated in the pump by fluid resistance when the solution flows through the column 54. The magnitude of the pressure is varied by the diameter of the column and the flow rate of the solution.

Hereafter, in this embodiment, a section including the first plunger 2 and the actuator for driving the first plunger 2 is referred to as "a large pump" and a section including the second plunger 3 and the actuator for driving the second plunger 3 is referred to as "a small pump".

Figure 2:
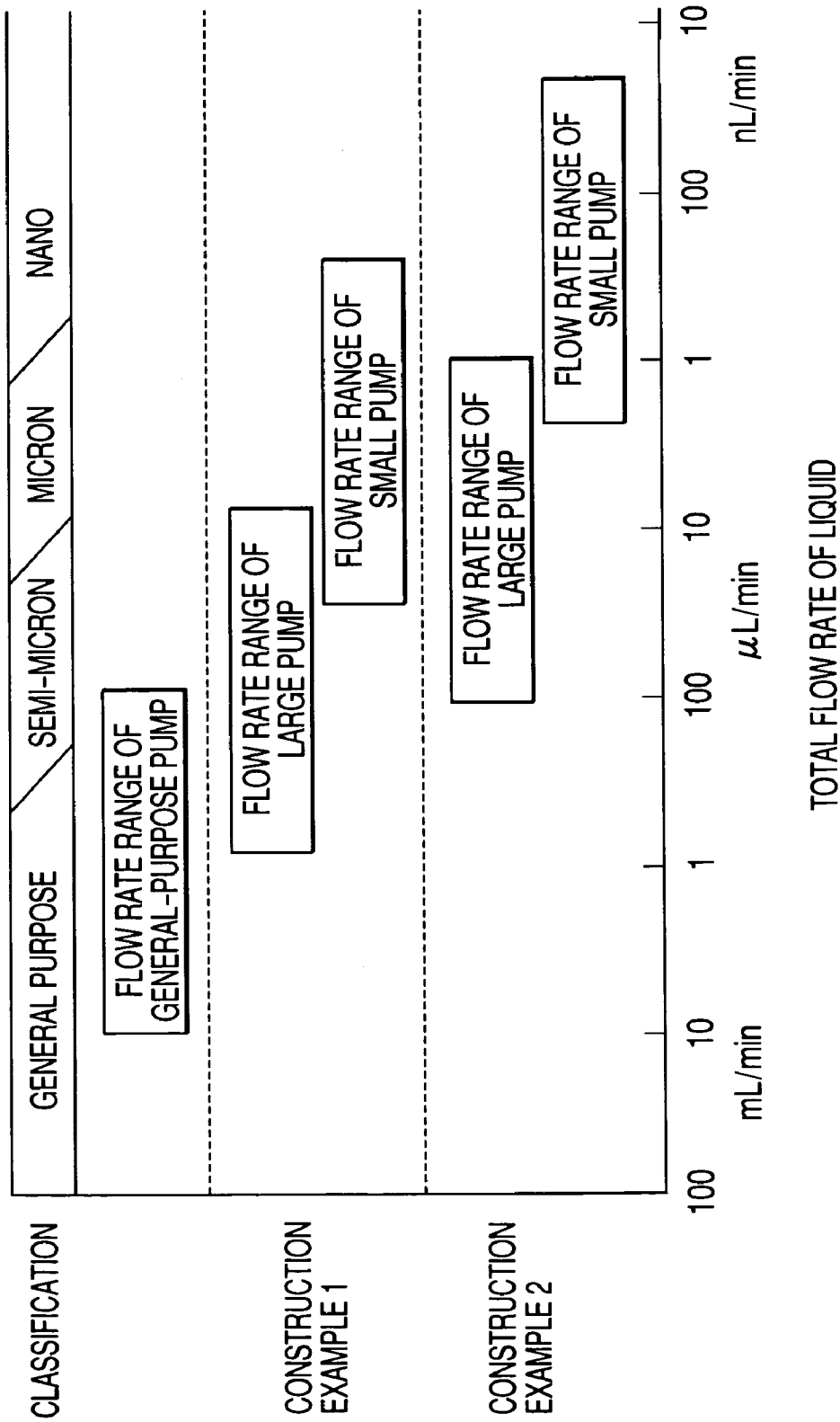
FIG. 2 is a chart to show the flow rate range of the pump for liquid chromatography of the invention.

Next, FIG. 2 is a chart to show the flow rate range of the pump for liquid chromatography and its classification. In the invention, a pump for liquid chromatography that feeds liquid at an extremely small flow rate of a semi-micron-liter per minute or less such as micron-liter per minute ($\mu$L/min) and nano-liter per minute (nL/min) is an object. As can be seen from one example of the flow rate range of a general-purpose pump shown in FIG. 2, the ratio of a maximum flow rate to a minimum flow rate is usually about 100 at most because of limitations of the number of revolutions and the rotational accuracy of the motor. Hence, when the flow rate is set in a region of $\mu$L/min or nL/min, a maximum flow rate naturally becomes small. For this reason, there are presented a problem that it takes much time to fill solvent into the passage in the measurement system on the downstream side of the pump at the startup of test and a problem that bubbles remaining in the pump cannot be easily discharged. In particular, when the bubbles remain in a pressure chamber, there is presented a problem that even if the plunger reciprocates, it only compresses or expands the bubbles and can not discharge the smallest amount of liquid or discharges liquid at an extremely low flow rate, which makes it impossible to perform measurement with high accuracy.

Therefore, this embodiment is so constructed as to feed liquid at an extremely low flow rate by the small pump including the section of the second plunger 3 and to fill the solvent and to discharge the bubbles by the large pump including the section of the first plunger 2 at the startup of test.

As shown in construction examples 1, 2 in FIG. 2, the flow rate range of the small pump is set so as to cover a region of $\mu$L/min or nL/min, whereas the flow rate range of the large pump is set in a larger flow rate region than this to make a maximum flow rate reach a general-purpose region and to make a minimum flow rate smaller than the maximum flow rate of the small pump. That is, the flow rate regions of both pumps are made to overlap each other. Here, since the flow rate is the product of the sectional area of the plunger and a speed thereof, the flow rate can be variably set by varying the diameter of the plunger, the rotational speed of the motor, and a speed reduction ratio.

Here, the total flow rate of liquid on a horizontal axis in FIG. 2 means the total flow rate of liquid at the time of a high-pressure gradient operation that will be described later. In the gradient operation, the flow rate is varied at from several tens steps to about 100 steps, so that the minimum flow rate that is a minimum resolution to be provided by the pump becomes smaller than this by one digit or two digits.

In the above construction, by use of FIG. 3, a method for operating the pump for liquid chromatography in accordance with the invention will be described. In FIG. 3, from the top, the displacement of the first plunger 2, the displacement of the second plunger 3, pressure at a pressure sensor 60, the flow rate of the large pump, the flow rate of the small pump, and the total flow rate passing through the discharge passage 11 are shown with respect to time on a horizontal axis.

First, when the bubbles in the pump are discharged and the solvent is filled as a preliminary stage of test, the discharge valve 52 is opened and the first plunger 2 is reciprocated at a high speed to feed liquid at a large flow rate. At this time, since the large pump is arranged on the upstream side, bubbles remaining in the second pressure chamber on the downstream side can be easily discharged. In particular, in the pump of the present embodiment, particular attention is paid so as to prevent bubbles from remaining in the pressure chamber as follows: a passage is constructed in such a way that the solvent is introduced from near the seal portion of the pressure chamber and is discharged from the tip of the pressure chamber to prevent the solvent from remaining in the pressure chamber, thereby preventing bubbles from reaming in the pressure chamber. With this, preparation for test can be completed in the same short time as in the general-purpose pump for liquid chromatography. In this regard, the second plunger 3 is at rest during this period and the flow rate is intermittent as shown in the chart but a pulsating flow rate in this mode does not affect measurement accuracy and hence presents no problem.

Next, when the operation goes into a normal operation, the discharge valve 52 is closed and the second plunger 3 is pushed into the second pressure chamber 13 at a low speed to feed the liquid at a low flow rate. During this period, the first plunger 2 is basically at rest and only the small pump feeds the liquid. Next, when the second plunger 3 reaches near full stroke, it is pulled back at a maximum high speed and the first plunger 2 is pushed into the first pressure chamber in synchronization with the pullback to cancel the pulsation of the flow rate. In this manner, the first plunger 2 and the second plunger 3 are controlled in such a way as to keep a total flow rate always at a constant flow rate. That is, if the sum of absolute values of Q1 and Q2 in the chart is made equal to Q3, the liquid can be always fed at a constant flow rate. In FIG. 2, the reason why the flow rate range of the large pump overlaps the flow rate range of the small pump is to cancel the respective flow rates to eliminate the pulsation of the flow rate. The larger the maximum flow rate of the large pump, the larger the effect. However, since there is a limitation that a minimum flow rate needs to be equal to the sum of absolute values of Q1 and Q2, the maximum flow rate is naturally limited. Hence, if the second plunger is pulled back as quickly as possible to increase Q2, the minimum flow rate of the large pump can be increased and at the same time the maximum flow rate can be also increased.

In this regard, while the second plunger 3 is pushed into the second pressure chamber 13, the first plunger 2 is basically at rest and only the small pump produces flow rate but a method for displacing the first plunger 16 by Xini, as shown in the chart, when pressure is increased to a predetermined value Pset at the start, is effective. To increase the pressure to the predetermined value, the plunger needs to be pushed into the pressure chamber to a certain degree because of the compressibility of fluid and the deformation of seals. However, since the second plunger 3 is set at a small flow rate, the second plunger 3 is set at a small diameter or a short stroke and hence when the pressure is increased to the Pset by the second plunger 3, most portion of stroke is consumed only for increasing the pressure and also the time that elapses until the pressure is increased to the Pset is elongated. For this reason, it can be said that increasing pressure at the startup is more effectively performed by the large pump.

Figure 3:
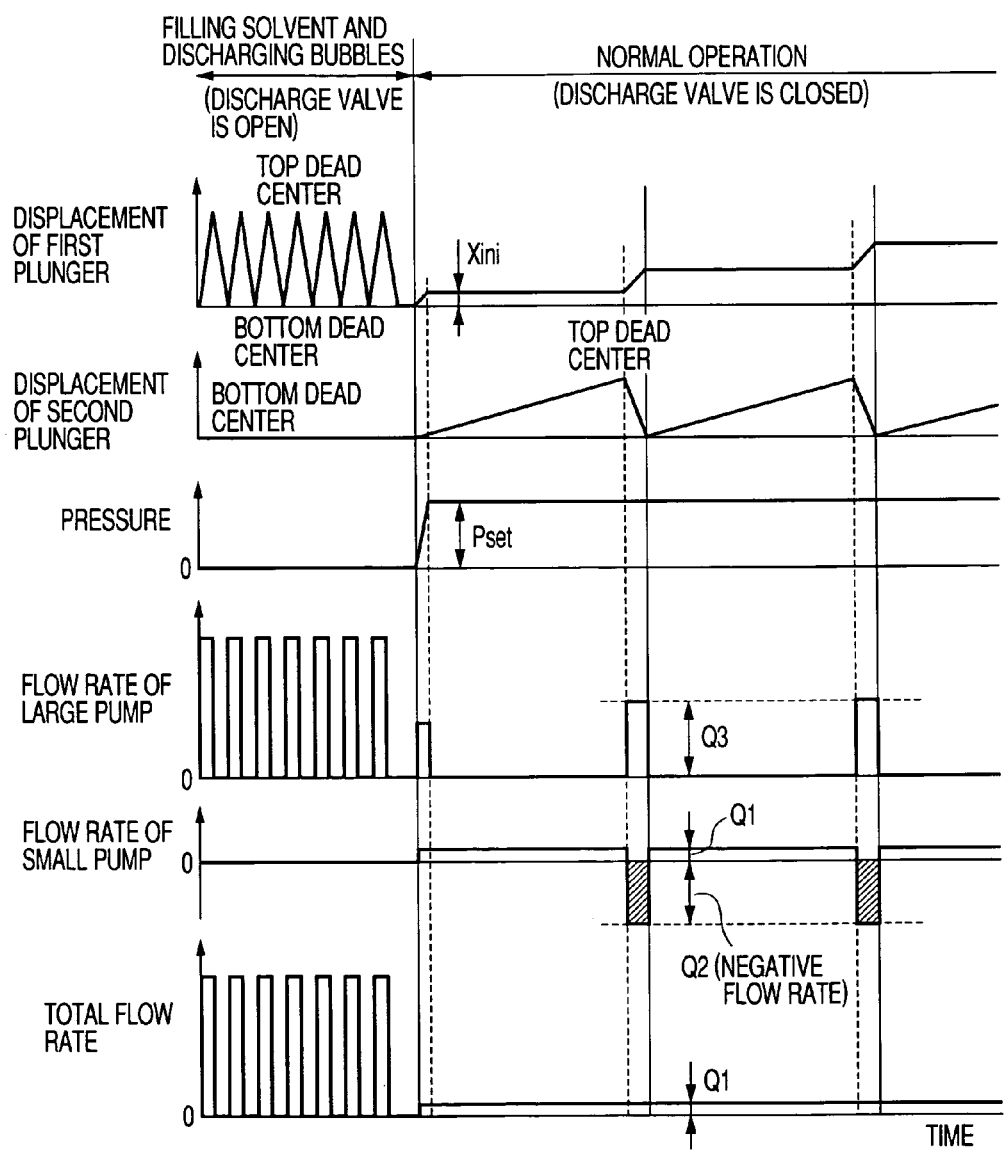
FIG. 3 is a chart to show one example of a method for driving the pump for liquid chromatography of the invention.

The operation method shown in FIG. 3 employs the following operation pattern: the first plunger is pushed several times in accordance with the pullback stroke of the second plunger and then when the first plunger reaches near the full stroke, it is pulled back near to a bottom dead center while the second plunger is being pushed. This method is a construction in which pressure in the pressure chamber 1 is kept at the same high pressure as pressure in the pressure chamber 2 for a long time. Hence, this method has a feature that since the pressures are equal to each other, pulsation when the second plunger is pulled back can be easily compensated but presents a problem that the dead volume of the pressure chamber 1 becomes large. It is generally know that the reproducibility during the gradient operation is decreased, when the dead volume is large.

Figure 4:
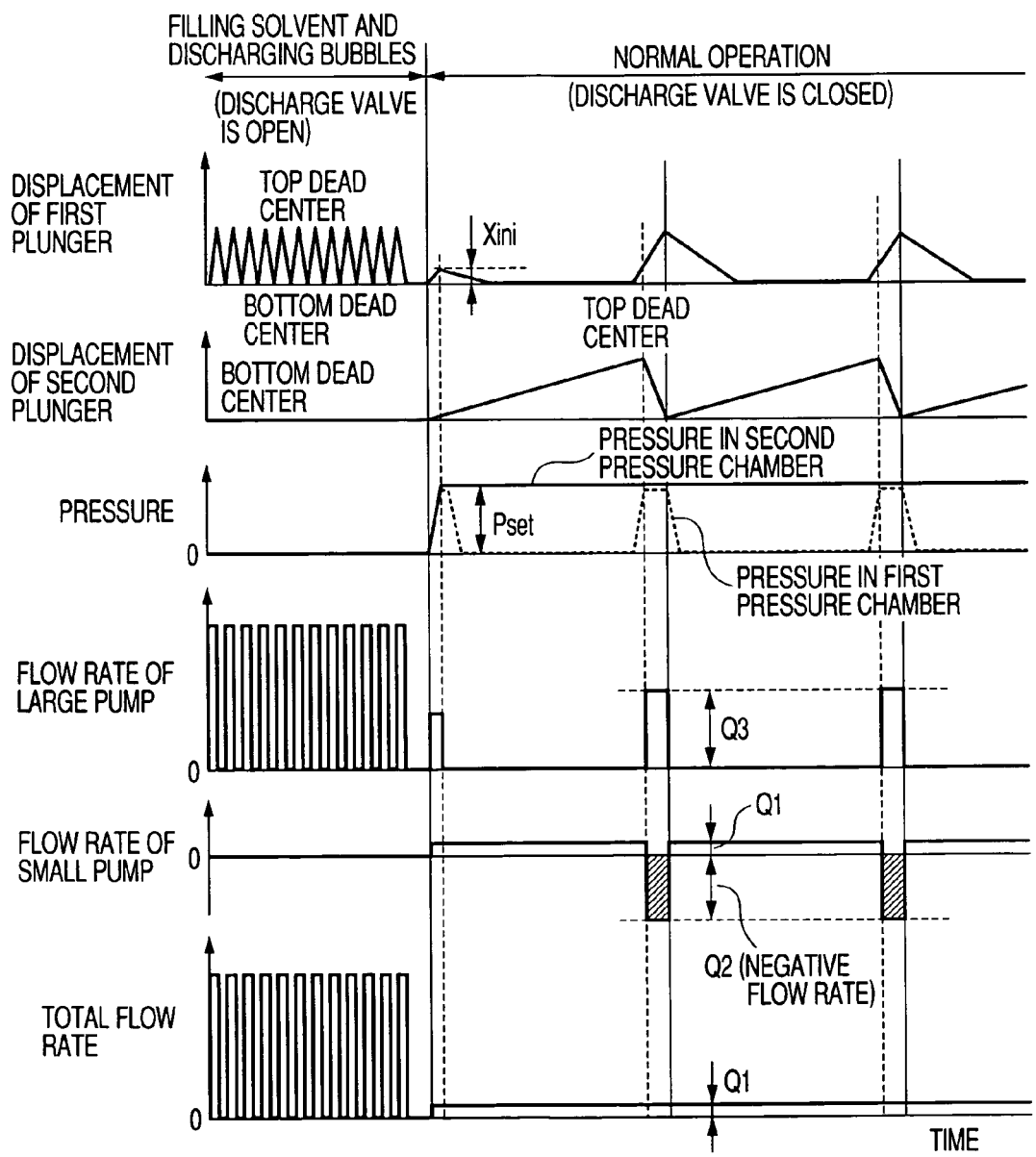
FIG. 4 is a chart to show one example of a method for driving the pump for liquid chromatography of the invention.

For this reason, the operation method shown in FIG. 4 is constructed in such a way that the stroke of the first plunger is reduced to reduce the dead volume and that while the second plunger reciprocates one time, the first plunger also reciprocates one time. Since the stroke is reduced and a cycle of reciprocation can be shortened by the same amount, the same large flow rate as in FIG. 3 can be acquired at the startup. In this case, there is provided a pattern that the pressure in the first pressure chamber 12 is decreased at the time of suction when the first plunger is pulled back and is increased when the first plunger is pushed. Hence, attention needs to be paid to the following: the pressure in the first pressure chamber needs to be made nearly equal to the pressure in the second pressure chamber 13 to prevent the occurrence of a pulsating flow rate. Hence, in the embodiment shown in FIG. 4, by starting pressing in the first plunger a little earlier than timing when the second plunger starts to return, when the second plunger starts to return, the pressures in both pressure chambers are made nearly equal to each other.

Figure 5:
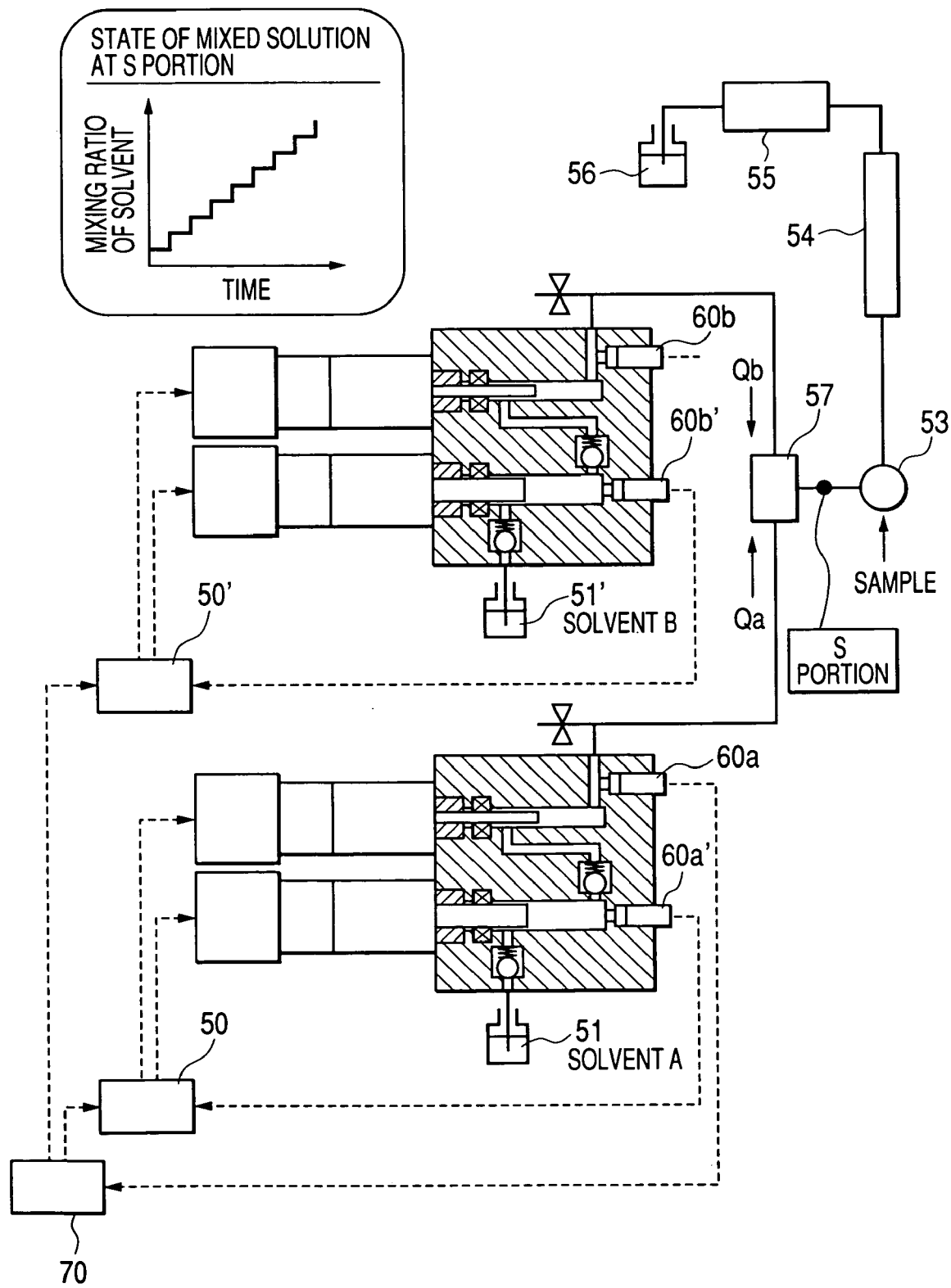
FIG. 5 is an illustration to show one example of a system construction using the pump for liquid chromatography of the invention.

Next, FIG. 5 shows an example in which two pumps for liquid chromatography in accordance with the invention are used to construct a high-pressure gradient system. A gradient operation means a method for varying the mixing ratio of two kinds of solvents A, B stepwise with the passage of time and a test is conducted by varying the ratio of Qa to Qb while keeping the total amount of flow rate of liquid (=Qa+Qb) at the same amount.

Figure 6:
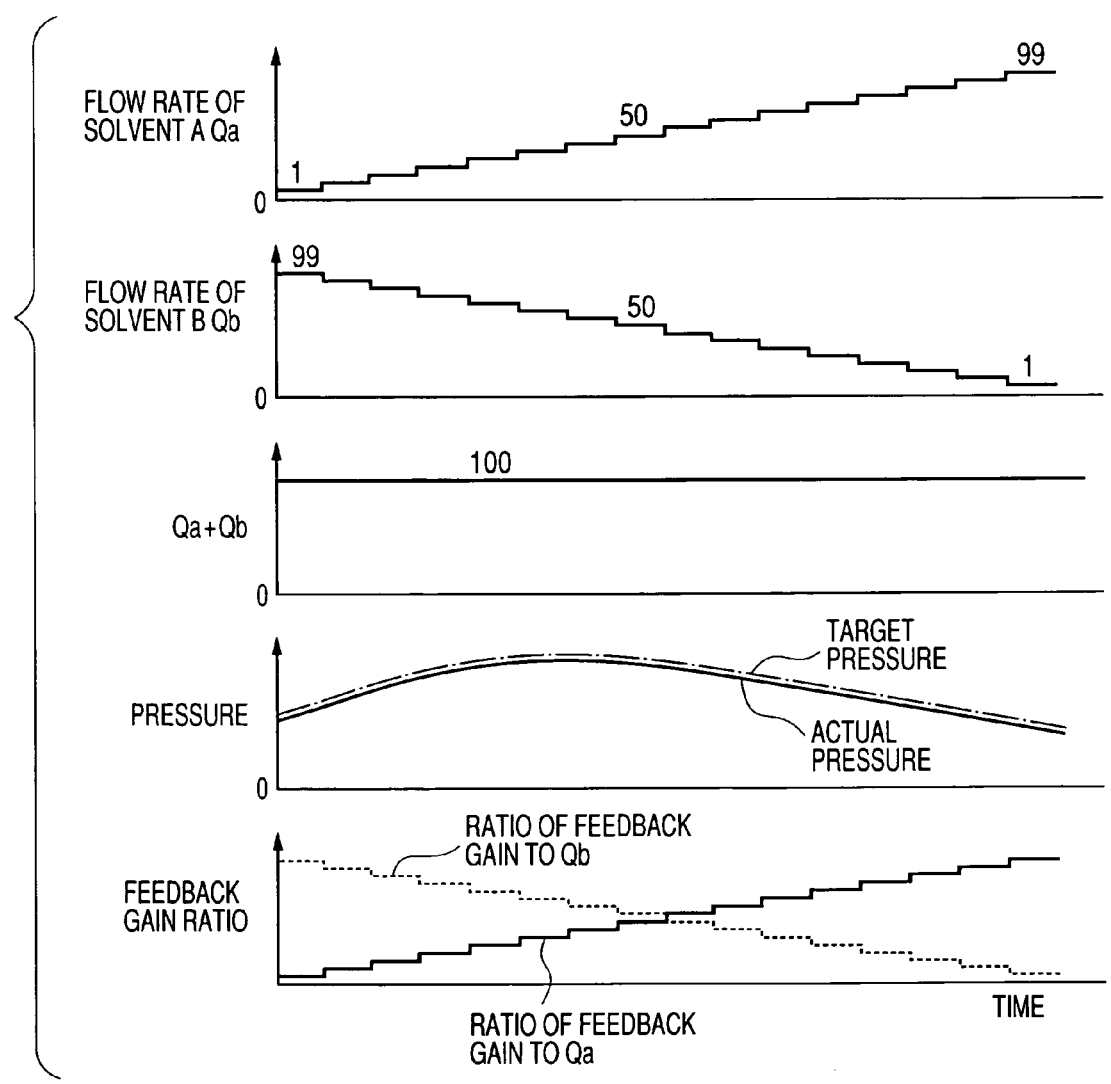
FIG. 6 is a chart to show one example of a method for driving the pump for liquid chromatography of the invention.

FIG. 6 shows that the respective elements vary with time in the gradient operation. Assuming that (Qa+Qb) is kept at a constant value of 100, the mixing ratio is started at first from Qa:Qb=1:99 and then is sequentially varied to 2:98, 3:97, . . . , 50:50, . . . , and 99:1. This shows a case where the mixing ratio is varied by 100 steps and assuming that the total amount of flow rate of liquid is 1 μL/min, the minimum flow rate and resolution of flow rate need to be 1/100 of this value, that is, 10 nL/min. It has been known that as shown in the charts in FIG. 6, even if the liquid is flowed at a constant flow rate, the composition of the fluid is varied by the mixing ratio, so that fluid resistance when the liquid passes through the column is varied to vary the discharge pressure of the pump by about 1.5 to 2 times at the maximum. For this reason, when it is intended to keep the pressure at a constant value, on the contrary, the flow rate is varied.

On the other hand, since the relationship between the mixing ratio and pressure variation is previously known from past experimental data, a pressure variation curve in a case where the flow rate is constant can be predicted. Hence, if the theoretical value of this pressure variation curve is made a target pressure and a pressure sensor signal is fed back to drive the pump to match an actual pressure with the target pressure, a constant total flow rate of liquid can be acquired with high accuracy. To be specific, the signal of the pressure sensor 60a in FIG. 5 is fed back to the main controller 70 to control the controllers 60, 60' of the respective pumps to make the pressure follow the target pressure. In this respect, since the discharge passages of both pumps communicate with each other via a mixer 57, the pressure is almost equal at any portions and hence any one of the pressure sensors 60a, 60b can be used.

If the actual pressure is lower than the target pressure, the total flow rate of liquid (=Qa+Qb) is decreased and hence the number of revolutions of the motor needs to be increased to increase the flow rate. However, it can not be determined from the information of one pressure sensor which of Qa and Qb is decreased. If it is determined that Qb is decreased and Qb is corrected in spite of the fact that Qa is actually decreased, on the contrary, the accuracy of the mixing ratio deteriorates. This is a problem that is called mutual interference in the gradient motion.

To avoid this mutual interference, in this embodiment, Qa and Qb are corrected on the assumption that Qa and Qb are decreased at the same rate. This can be realized by providing feedback gains proportional to a flow rate ratio as shown in the chart in FIG. 6. For example, the feedback gains of Qa and Qb in a case where the pump is operated at a flow rate ratio (Qa:Qb) of (20:80) are given as (20/100)×K, (80/100)×K, respectively, where K is a constant. If the total flow rate of liquid is 5 short and a proportional control is performed, command values of Qa and Qb are given as 20+(20/100)×K×5 and 80+(80/100)×K×5, respectively. For example, assuming that K is 1, the former command value becomes 21 and the latter command value becomes 84. According to this method, although a decrease in the mixing accuracy caused by the individual difference between the two pumps cannot be avoided, the problem of mutual interference can be avoided and hence a further decrease in the mixing accuracy can be prevented.

In this regard, since the discharge pressure varies with time, the pressures in the first pressure chambers of both pumps need to be varied in accordance with the varying discharge pressure. In particular, in a case where the pressure at the pressure sensor 60a (60b) is lower than the pressure in the first pressure chamber, the discharge check valve is opened, whereby the solvent in the first pressure chamber flows into the second pressure chamber to increase the flow rate of liquid. For this reason, in this embodiment, the pressure sensor 60a' (60b') is provided in the first pressure chamber of each of both pumps and the signal of the pressure sensor is fed back to the controller 50 (50') to drive the first plunger to thereby control the first plunger in such a way that the pressure in the first pressure chamber is equal to the discharge pressure measured by the pressure sensor 60a (60b).

In the manner described above, there can be provided a high-pressure gradient system excellent in stable liquid feed and in mixing accuracy.

Figure 7:
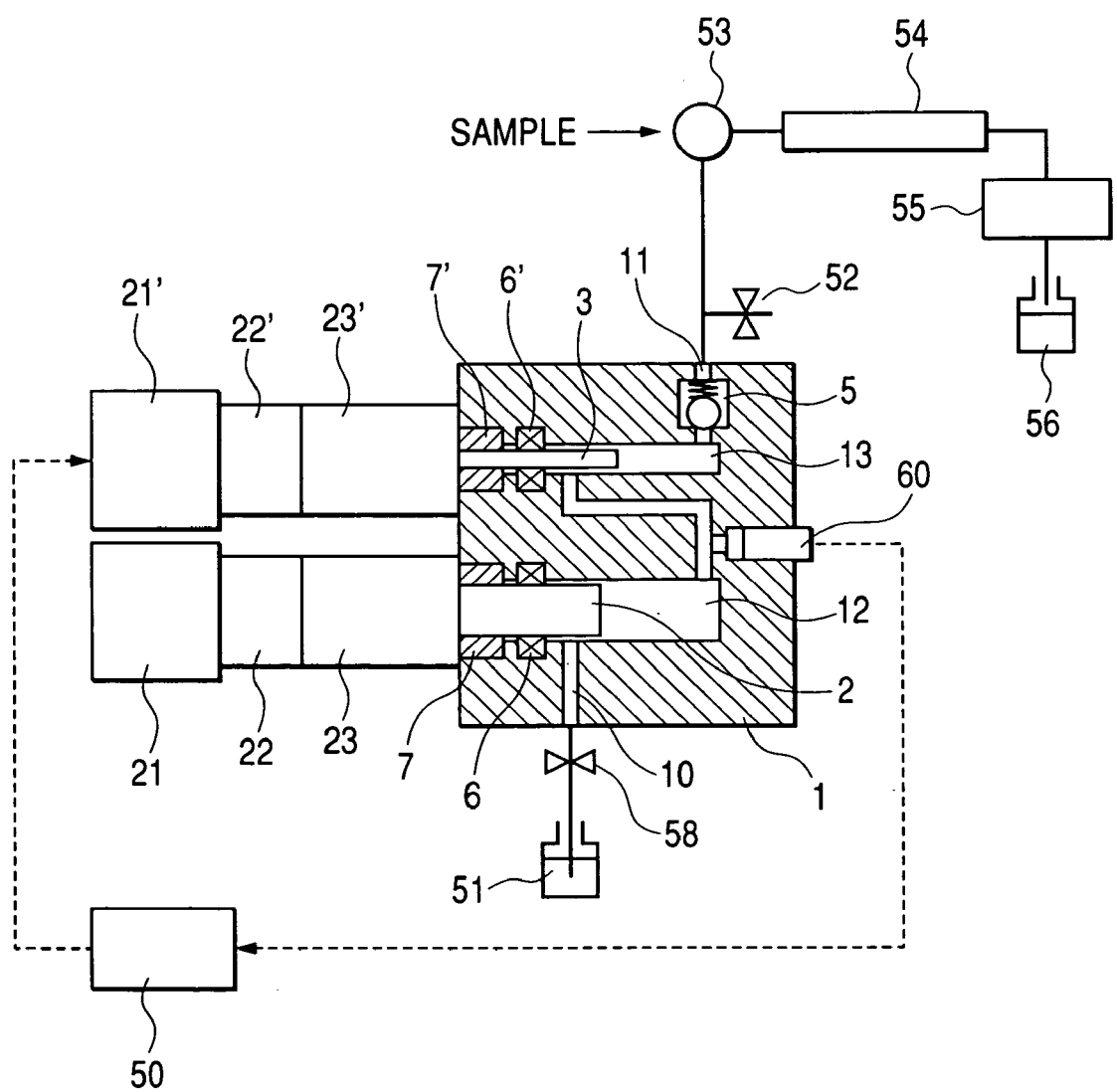
FIG. 7 is a longitudinal sectional view to show another embodiment of a pump for liquid chromatography of the invention.

Finally, FIG. 7 is another embodiment of a pump for liquid chromatography of the invention. This embodiment is different in the following points from the pump for liquid chromatography shown in FIG. 1.

(1) A suction check valve is not provided and a suction part is provided with a stop valve 58 in place of the suction check valve.

(2) The discharge check valve 5 is relocated to the downstream side of the second pressure chamber 13.

The present pump has a construction in which the liquid is fed at a low flow rate by the second plunger 3. As the present pump is thought a syringe pump of one stroke type in which measurement is finished when the second plunger 3 reaches its full stroke.

Figure 8:
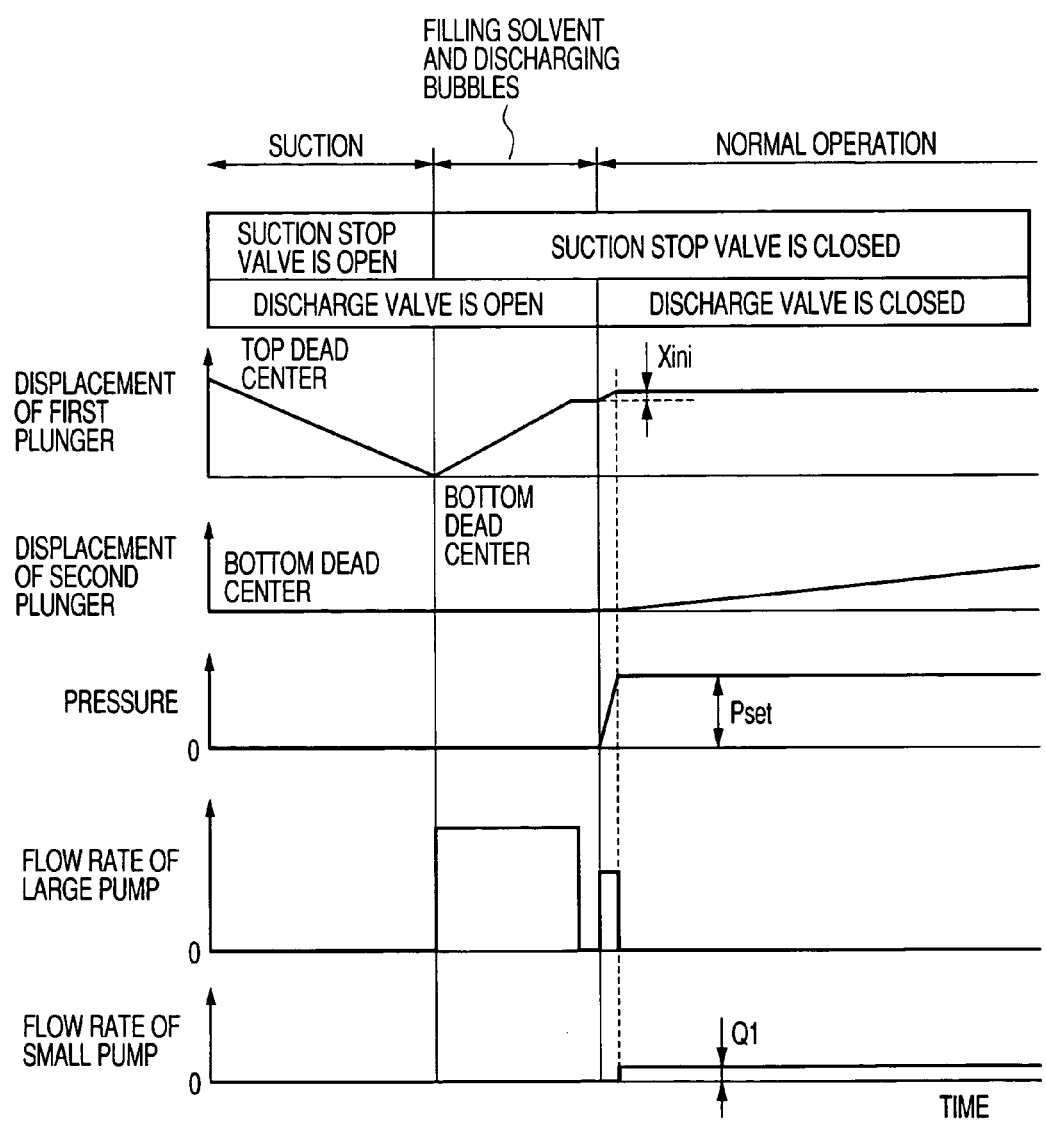
FIG. 8 is a chart to show one example of a method for driving liquid chromatography of the invention.

In FIG. 8 is shown one example of a method for operating the present pump. At first, the first plunger 2 is set near the top dead center and the second plunger 3 is set near the bottom dead center and both of the suction stop valve 58 and the discharge valve 52 are opened. The first plunger 2 is pulled back from this state to suck the solvent 51. When the first plunger 2 finishes sucking the solvent 51, the suction stop valve 58 is closed and the first plunger 51 is pushed into the first pressure chamber 12 to feed liquid at a large flow rate to thereby fill the solvent 51 into the pump while discharging bubbles in the pump. Needless to say, the displacement volume of the first plunger is large enough to fill the solvent into the measurement system on the downstream side by one stroke. Then, when the operation goes to a normal operation, the first plunger 2 is displaced by Xini to increase the discharge pressure to the predetermined pressure Pset. After the discharge pressure is increased, the first pressure 2 is stopped and the second plunger 3 is pushed into the second pressure chamber 13 at a low speed to feed the solvent at a low flow rate of Q1.

In this construction, measurement is finished at the time when the second plunger 3 is pushed to full stroke and the second plunger 3 is not pulled back, so that pulsation hardly occurs inherently. Moreover, since the solvent is sealed by the suction stop valve 58, leakage can be greatly reduced as compared with the check valve. Hence, this construction has a feature that the flow rate fed by the plunger can be discharged with extremely high accuracy. Although the operation is finished by one stroke, the operation can be performed continuously for 24 hours in a region where the total flow rate of liquid is nL/min. Therefore, it can be said that the pump for liquid chromatography shown in FIG. 7 is effective especially when a specification of a lower flow rate of nL/min is realized.

In this regard, when the flow rate is an extremely low flow rate of this level, the actuator is not necessarily of the type of (motor+direct–acting mechanism) but, for example, a piezoelectric actuator or an actuator that controls displacement by a temperature control using the thermal expansion of metal may be applicable.

Moreover, in this embodiment, one pump body is provided with two pressure chambers and the pressure chambers are connected to each other by a passage. However, it is also recommended that pump heads are separately provided and connected to each other by a piping to construct a system. With this, the pump can be easily disassembled and hence maintenance work such as seal exchange can be easily performed. Moreover, an advantage of improving the ease with which the parts are laid out can be provided.

Here, a material of high hardness such as stainless steel, ruby, or ceramics is generally used for the check valve of the pump for liquid chromatography from the viewpoint of chemical resistance and durability. However, in the check valve of this kind, a minute leakage cannot be avoided even in a state where the check valve is closed and becomes a factor that reduces a liquid feed accuracy, in particular, in the case of feeding liquid at an extremely low flow rate. In the pump for liquid chromatography in accordance with the invention shown in FIG. 1, the reduction of the flow rate of liquid leaking from the second pressure chamber 13 to the first pressure chamber 12 through the discharge check valve 5 leads to the improvement of liquid feed accuracy.

Figure 9:
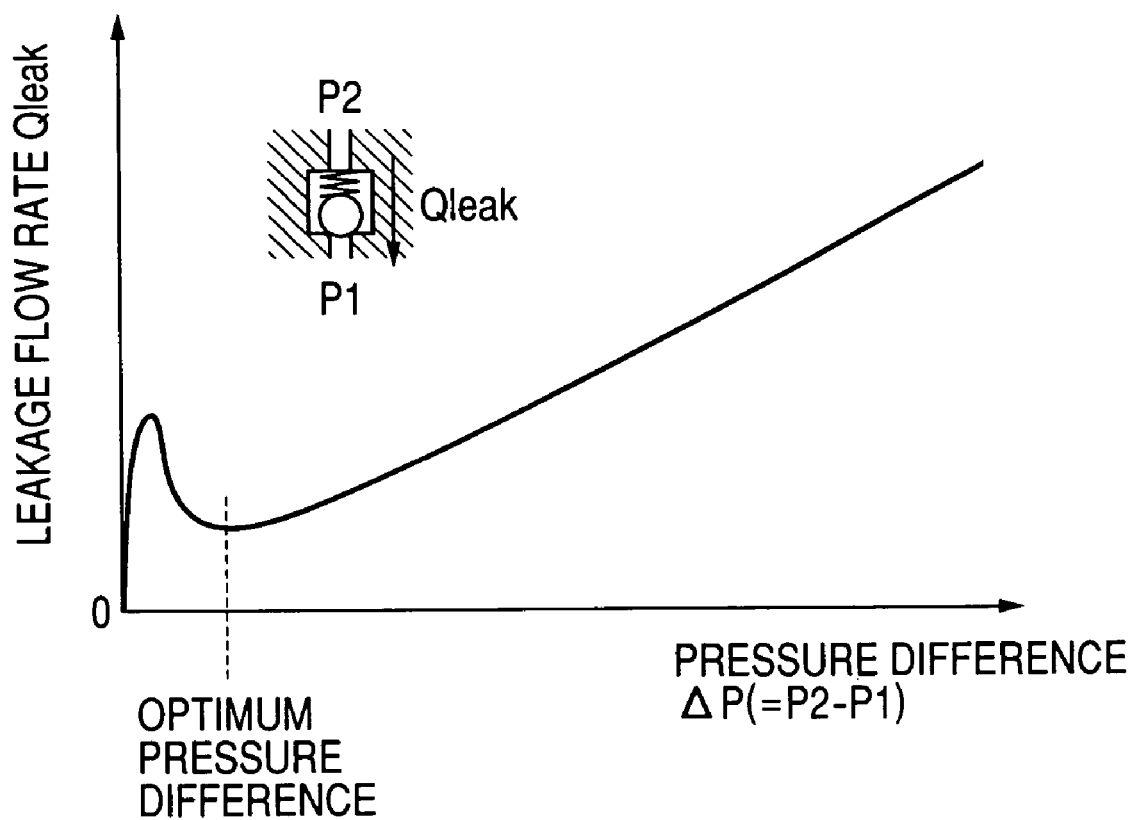
FIG. 9 is a graph to show one example of leakage characteristics of a check valve.

FIG. 9 shows an example of leakage characteristics of a check valve made of a material of high hardness. In a case where a pressure difference across the check valve is very small, a valve body cannot be pressed onto a valve seat at a sufficient contact pressure and hence leakage increases. The leakage becomes a minimum value at a position where the pressure difference becomes a certain value and from this position, the leakage increases as the pressure difference increases. That is, to reduce the leakage from the check valve, controlling the pressure difference at an appropriate value is effective. In the pump for liquid chromatography of the invention, by controlling the amount of push of the first plunger into the first pressure chamber, the pressure difference can be controlled. This will be described by a specific example.

Figure 10:
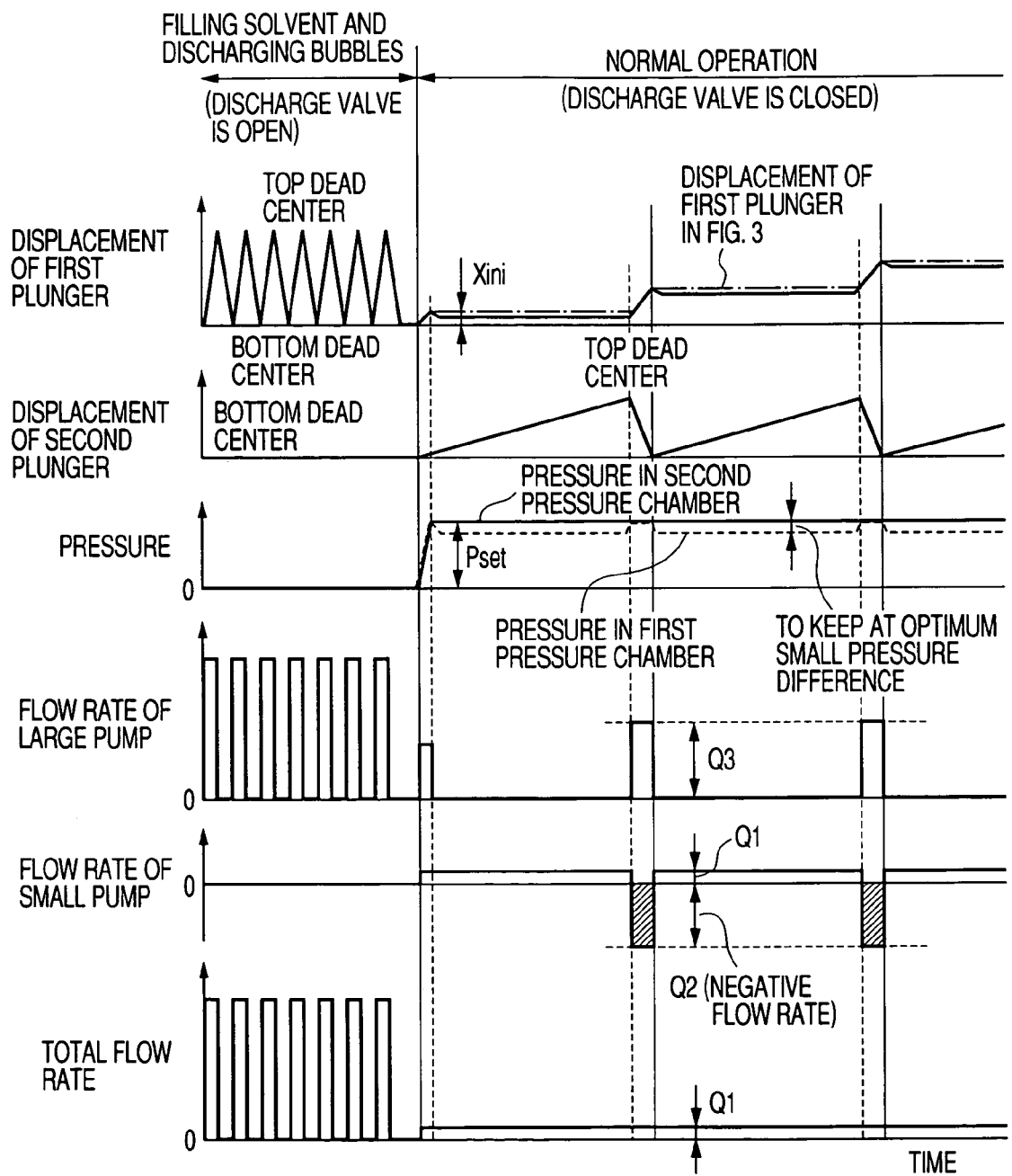
FIG. 10 is a chart to show one example of a method for driving the pump for liquid chromatography of the invention.

An operation method shown in FIG. 10 is one in which logic of reducing leakage from the check valve is added to the operation method shown in FIG. 3 and is different from the operation method shown in FIG. 3 in the way the first plunger is moved. As shown by a single dot and dash line, in FIG. 3, the first plunger is at rest while the second plunger feeds the liquid. On the other hand, in FIG. 10, the first plunger is slightly pulled back to reduce the pressure in the first pressure chamber to control the pressure difference between the first pressure chamber and the second pressure chamber to an optimum pressure difference (see FIG. 9) that minimizes the leakage from the check valve. Since the pressure difference is hardly provided in FIG. 3, the sealing contact pressure of the check valve is not sufficient and hence leakage might increase. However, if the present operation method is used, the leakage of the check valve is minimized and the liquid is fed at a low flow rate with high accuracy.

Figure 11:
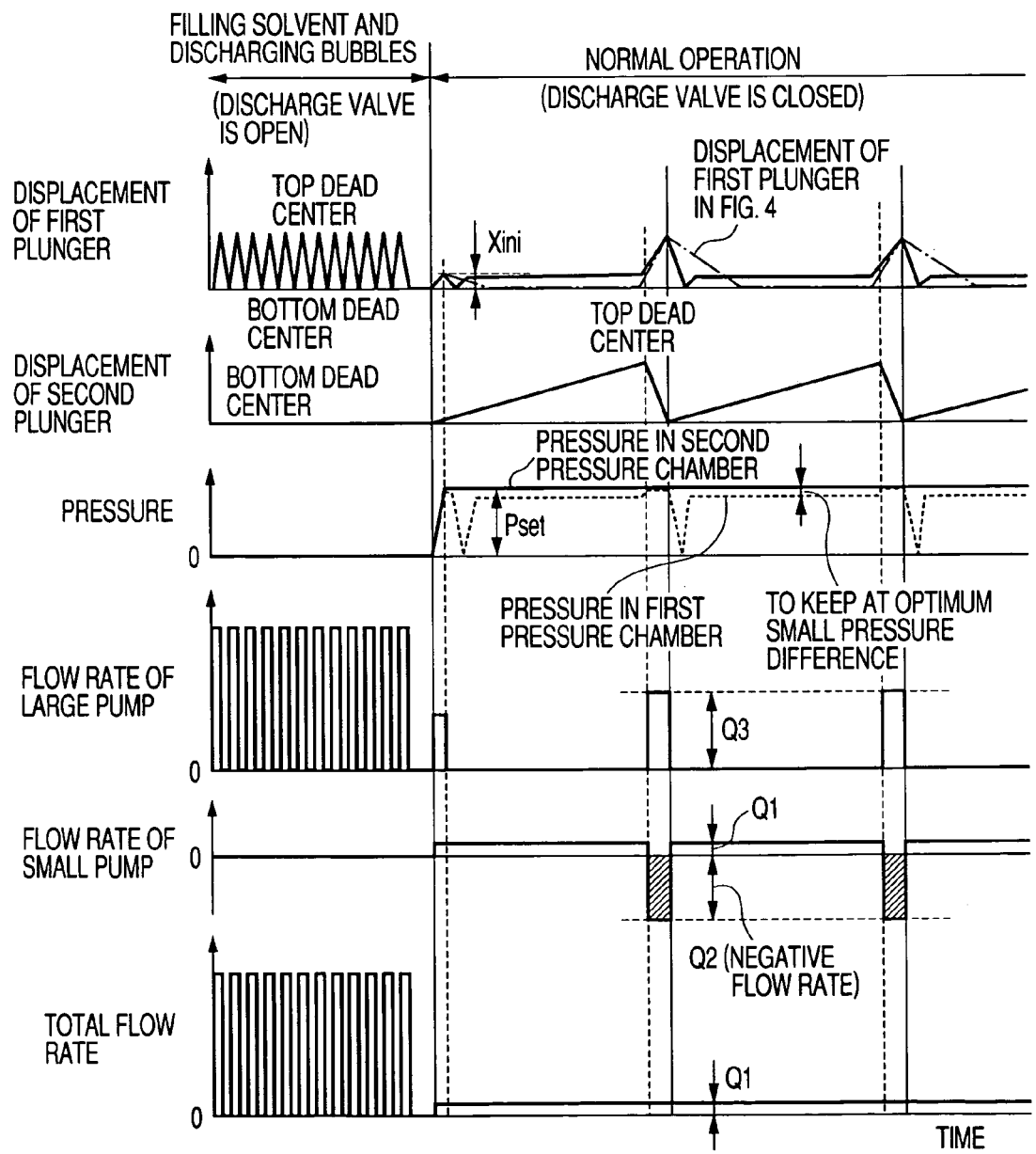
FIG. 11 is a chart to show one example of a method for driving the pump for liquid chromatography of the invention.

Next, an operation method shown in FIG. 11 is one in which logic of reducing leakage from the check valve is added to the operation method shown in FIG. 4. On the contrary to the case in FIG. 9, by pushing the first plunger slightly while the second plunger feeds the liquid, the pressure in the first pressure chamber is increased to reduce the pressure difference between the first pressure chamber and the second pressure chamber to control the pressure difference to the optimum pressure difference that minimizes the leakage from the check valve. Further, as shown by a single dot and dash line, in FIG. 4, the first plunger is pulled back at a slow speed to suck the liquid, but in FIG. 11, the first plunger is quickly pulled back to shorten a suction time to elongate the time when the optimum pressure difference is obtained to thereby reduce the leakage from the check valve to the maximum. However, if the first plunger is pulled back too quickly, bubbles are made in the solvent by negative suction pressure. Hence, it is necessary to make sure a limit speed not to make the bubbles and to determine the pullback speed of the first plunger. By this operation method, leakage from the check valve can be substantially decreased as compared with the case in FIG. 4 and the liquid can be fed at a low flow rate with high accuracy.

Moreover, since the durability of the check valve can be improved by reducing the pressure difference, a check valve made of resin which could not be used in the past can used. The durability of the check valve is none other than the durability of a sealing face. If the pressure difference decreases, the sealing pressure also decreases, which leads to the improved durability of the sealing face. Since the check valve made of resin causes a significantly small mount of leakage as compared with the check valve constructed of a material of high hardness such as stainless steel or ruby, the application of this check valve make it possible to feed liquid at an extremely low flow rate with higher accuracy.

Here, factors to reduce a liquid feed accuracy include not only the leakage from the check valve but also a reduction in the feed accuracy of the plunger. Factors to reduce the feed accuracy of the plunger include variations in the rotational angle of the motor, the play and backlash of a mechanical system, and variations in the synchronous control of both plungers. As for the motor, a stepping motor is usually used and hence if only the number of pulses is correctly produced, the rotational angle will not vary. In a state where load is applied to the mechanical system in one direction, the play and backlash of the mechanical system do not present any problem but have an effect on the feed accuracy of the plunger when the load applied to the mechanical system is changed in direction. The pump for liquid chromatography of the invention undergoes this effect in a case where the second plunger is pulled back and the first plunger is pushed into the first pressure chamber correctly in synchronization with the pullback of the second plunger. Since high pressure is always applied to the second plunger, the second plunger does not suffer the effect. However, the first plunger is susceptible to the effect of the play and backlash because the load applied to the first plunger is changed in direction by a rapid change in pressure. After all, this effect causes variations in the synchronous control of both plungers to vary the flow rate momentarily.

In the pump for liquid chromatography, the second plunger is pulled back in a short time to reduce the effect that momentary variations in the flow rate during this period have on the total amount of feed of liquid. However, this is not always adequate for feeding the liquid at an extremely low flow rate in the range of from μL/min to nL/min with high accuracy.

Figure 12:
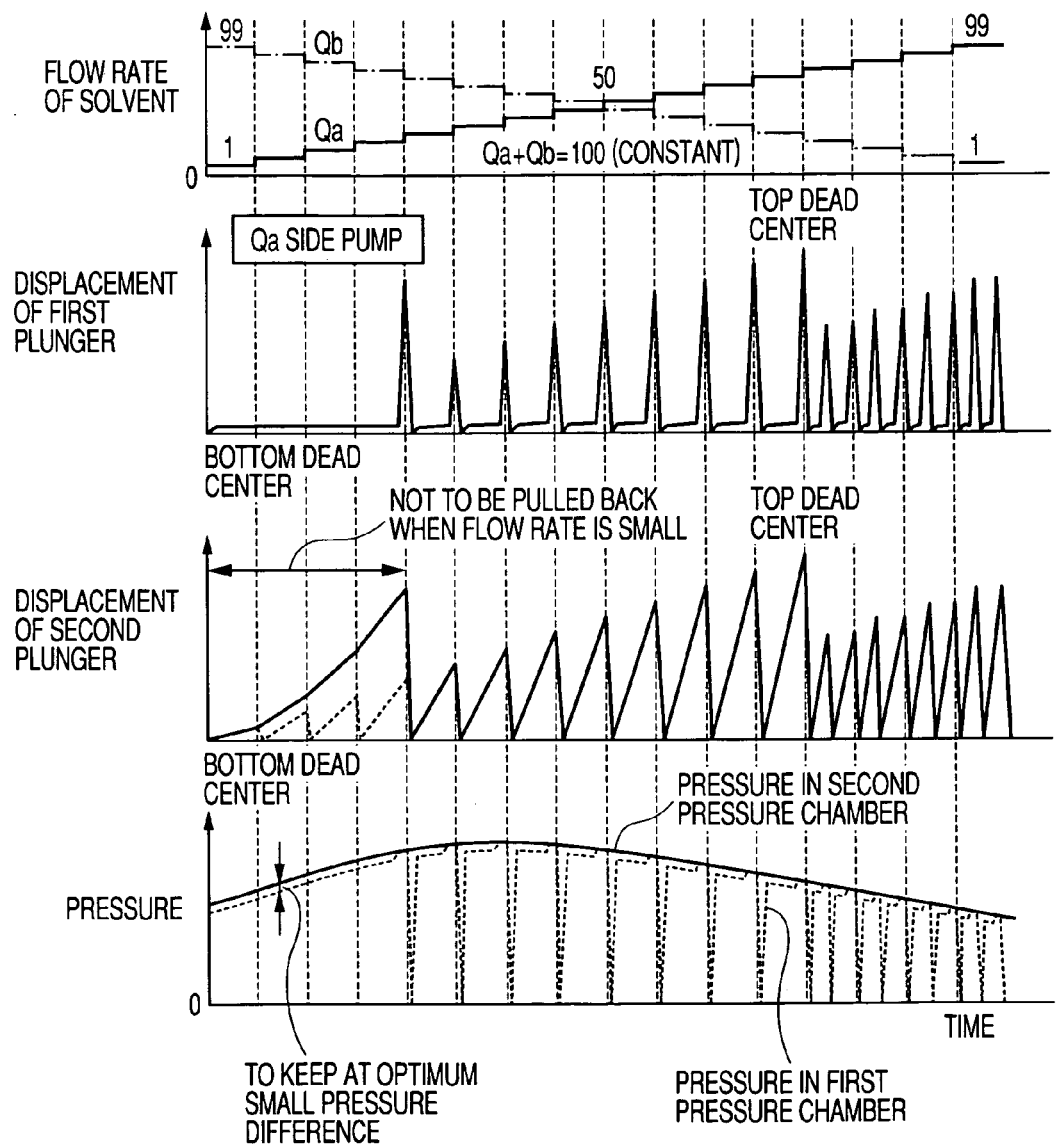
FIG. 12 is a chart to show one example of a method for driving the pump for liquid chromatography of the invention.

Hence, as shown in FIG. 12, a method not to pull back the second plunger at a low flow rate is effective. FIG. 12 shows one example of the operation method in the gradient operation mode described in FIG. 5 and FIG. 6 and details the operation of the plunger of the pump on the Qa side. In the process of increasing Qa gradually in the gradient operation, while the flow rate is small, the second plunger is not pulled back as shown by a dotted line but is moved in one direction. This operation can prevent the flow rate from being varied by the variations in the synchronous control of the plungers and hence can feed the liquid at an extremely low flow rate with extremely high accuracy. Further, as described above, during this period, the pressure in the first pressure chamber is controlled by the first plunger to hold the optimum pressure difference to minimize the leakage from the check valve. With this operation, the liquid feed accuracy can be further improved to feed the liquid at an extremely low flow rate in the range of from μL/min to nL/min with sufficiently high accuracy.

Figure 13:
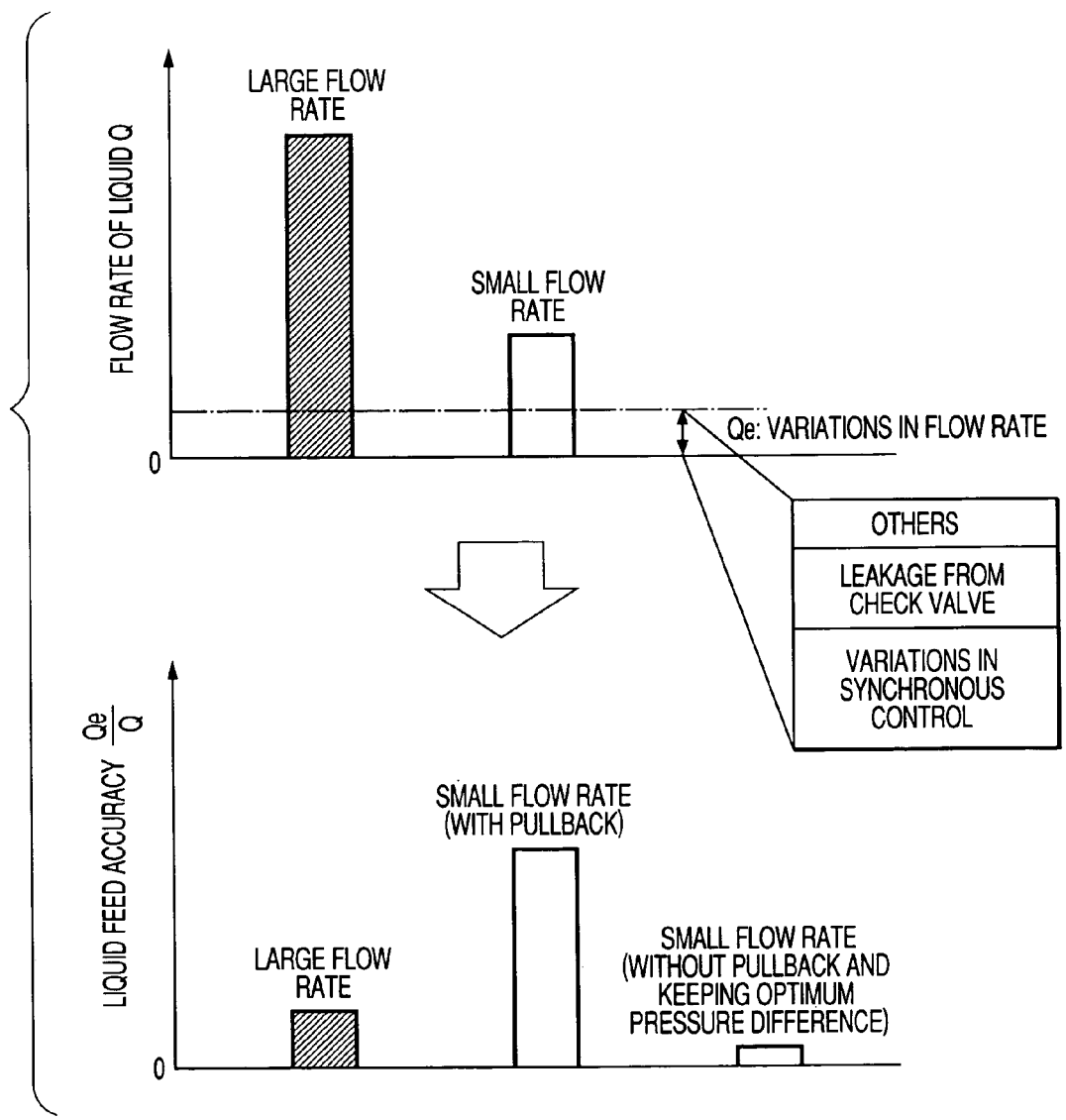
FIG. 13 is a chart to show the effect of a method for driving the pump for liquid chromatography of the invention.

FIG. 13 shows the effect of this operation method. Since a certain amount of variations Qe in flow rate is caused irrespective of the amount of flow rate by the variations in the synchronous control of the plungers and the leakage of the check valve and the effect of Qe becomes larger as the flow rate becomes smaller, the liquid feed accuracy is reduced. Hence, in a case where the flow rate is low, the second plunger is not pulled back and the first plunger is controlled to keep the optimum pressure difference. This operation eliminates the variations in the synchronous control of the plungers of the variations Qe and hence reduces leakage from the check valve to improve the liquid feed accuracy drastically.

According to the present invention, there can be provided a pump for liquid chromatography that can feed liquid at an extremely low flow rate in stable condition of low pulsation and not trapping bubbles and that can complete filling solvent and discharging bubbles in a short time at the startup of test. In addition, since leakage from the check valve can be minimized and the plunger can be driven with high accuracy, the liquid can be fed at a low flow rate with extremely high accuracy.

What is claimed is:

1. A pump for liquid chromatography comprising a pressure chamber communicating with an suction passage, a pressure chamber communicating with a discharge passage, and a first plunger and a second plunger that respectively reciprocate in the pressure chambers, wherein the first plunger is provided on an upstream side near to the suction passage and wherein the second plunger is provided on a downstream side near to the discharge passage, wherein the first and the second plungers are driven independently by separate actuators, respectively, wherein a maximum flow rate by the first plunger is larger than a maximum flow rate by the second plunger, and wherein a minimum flow rate by the first plunger is smaller than a maximum flow rate by the second plunger.

2. A pump for liquid chromatography comprising a first pressure chamber communicating with an suction passage and a middle passage, a first plunger reciprocating in the first pressure chamber, a suction valve provided in the suction passage, a discharge valve provided in the middle passage, a second pressure chamber formed on a downstream side of the discharge valve and communicating with the middle passage and a discharge passage, and a second plunger reciprocating in the second pressure chamber, wherein the first and the second plungers are driven independently by separate actuators, respectively, wherein a maximum flow rate by the first plunger is larger than a maximum flow rate by the second plunger, and wherein a minimum flow rate by the first plunger is smaller than a maximum flow rate by the second plunger.

3. The pump for liquid chromatography as claimed in claim 1 or claim 2, further comprising a drain valve provided on a downstream side of the discharge passage, wherein the drain valve is opened at startup of test and solvent is fed at a large flow rate by the first plunger to discharge bubbles remaining in the pressure chamber and at the same time to fill the solvent into a downstream passage and wherein the drain valve is then closed and the solvent is fed at a low flow rate by the second plunger.

4. The pump for liquid chromatography as claimed in claim 2, further comprising a drain valve provided on a downstream side of the discharge passage, wherein the drain valve is opened at startup of test and solvent is fed at a large flow rate by the first plunger to discharge bubbles remaining in the pressure chamber and at the same time to fill the solvent into a downstream passage, wherein the drain valve is then closed and the second plunger is pushed into the second pressure chamber at a slow speed to feed the solvent at a low flow rate, and wherein when the second plunger reaches near full stroke, the second plunger is pulled back at a high speed and the first plunger is pushed into the first pressure chamber in synchronization with the pullback of the second plunger to control a flow rate passing the discharge passage to a constant value at all times.

5. The pump for liquid chromatography as claimed in claim 4, wherein time required to push the second plunger in one reciprocation stroke is equal to or more than ten times time required to pull back the second plunger.

6. The pump for liquid chromatography as claimed in claim 4, wherein the amount of push of the first plunger into the first pressure chamber while the second plunger feeds the liquid is controlled to keep pressure in the first pressure chamber at pressure equal to or less than pressure in the second pressure chamber.

7. The pump for liquid chromatography as claimed in claim 6, wherein a surface of at least one of a valve seat and a valve body constructing the discharge valve is formed of material such as resin or rubber that has hardness lower than metal.

8. The pump for liquid chromatography as claimed in claim 4, wherein when the amount of flow rate of the pump is low particularly in a gradient operation, the second plunger is not pulled back except when the second plunger reaches a full stroke position.

9. The pump for liquid chromatography as claimed in claim 1 or claim 2, wherein a flow rate of liquid by the second plunger ranges from 0.1 nL/min to 50 µL/min.

10. The pump for liquid chromatography as claimed in claim 1 or claim 2, wherein product of sectional area and maximum speed of the first plunger is larger than product of sectional area and maximum speed of the second plunger, and wherein product of sectional area and minimum speed of the first plunger is smaller than product of sectional area and maximum speed of the second plunger.

* * * * *